United States Patent
Kobilka et al.

(10) Patent No.: US 7,947,807 B2
(45) Date of Patent: May 24, 2011

(54) METHOD FOR OBTAINING G PROTEIN-COUPLED RECEPTOR (GPCR) DIFFRACTION-QUALITY CRYSTALS EMPLOYING A MONOCLONAL ANTIBODY THAT BINDS TO THE THIRD INTRACELLULAR LOOP (IL3)

(75) Inventors: Brian Kobilka, Palo Alto, CA (US); Dan Rohrer, Los Gatos, CA (US); Peter Brams, Sacramento, CA (US); Asna Masood, Saratoga, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 74 days.

(21) Appl. No.: 12/284,245

(22) Filed: Sep. 19, 2008

(65) Prior Publication Data
US 2009/0148510 A1    Jun. 11, 2009

Related U.S. Application Data

(60) Provisional application No. 60/980,122, filed on Oct. 15, 2007.

(51) Int. Cl.
*C07K 14/00* (2006.01)
*C12P 21/08* (2006.01)
*B01D 9/00* (2006.01)

(52) U.S. Cl. ............... 530/350; 530/388.22; 23/300

(58) Field of Classification Search ........ None
See application file for complete search history.

(56) References Cited

U.S. PATENT DOCUMENTS 5,026,557 A    6/1991   Estis et al.

OTHER PUBLICATIONS

Day, P. W., et al., 2007, A monoclonal antibody for G protein-coupled receptor crystallography, Nat. Meth. 4(11):927-929.*
Baker, M., 2010, Making membrane proteins for structures: a trillion tiny tweaks, Nat. Meth. 7(6):429-434.*
Rosenbaum, D. M., et al., 2009, The structure and function of G-protein-coupled receptors, Nature 459:356-363.*
Chayen, N. E., and E. Saridakis, 2008, Protein crystallization: from purified protein to diffraction-quality crystal, Nat. Meth. 5(2):147-153.*
Mancia; et al., "Production and characterization of monoclonal antibodies sensitive to conformation in the 5HT2c serotonin receptor", PNAS, Mar. 13, 2007, 104(11):4303-4308.
Yohannan; et al., "The evolution of transmembrane helix kinks and the structural diversity of G protein-coupled receptors"PNAS, Jan. 27, 2004, 101(4):959-963.
Day; et al., "A monoclonal antibody for G protein-coupled receptor crystallography", Nat Methods, 2007 Nov. 4 (11)927-9.
Kobilka; et al., "G protein coupled receptor structure and activation", Biochim Biophys Acta, 2007 Apr. 1768(4) 794-807.
Whorton; et al., A monomeric G protein-coupled receptor isolated in a high-density lipoprotein particle efficiently activates its G protein.

* cited by examiner

*Primary Examiner* — Jeffrey S. Parkin
(74) *Attorney, Agent, or Firm* — Bozicevic, Field & Francis LLP; James S. Keddie

(57) ABSTRACT

An antibody that specifically binds a three dimensional epitope on the IC3 loop of a GPCR is provided. The antibody may be employed in a method that comprises: contacting a GPCR with a monovalent version of the antibody binding conditions to form a complex; and crystallizing the complex.

8 Claims, 8 Drawing Sheets
(3 of 8 Drawing Sheet(s) Filed in Color)

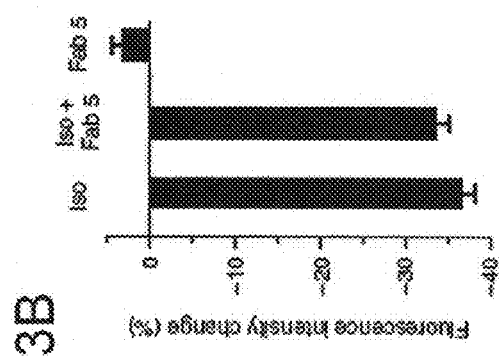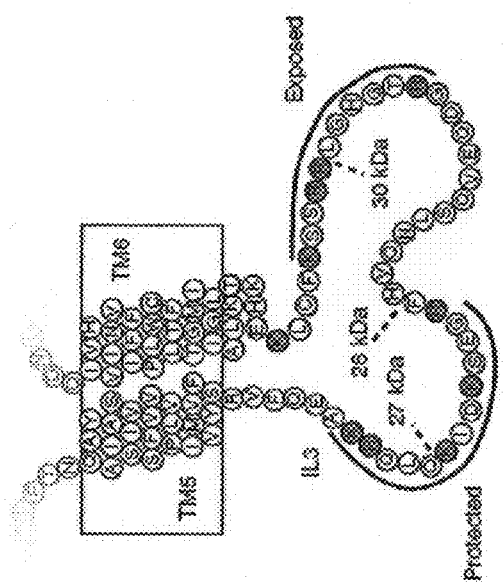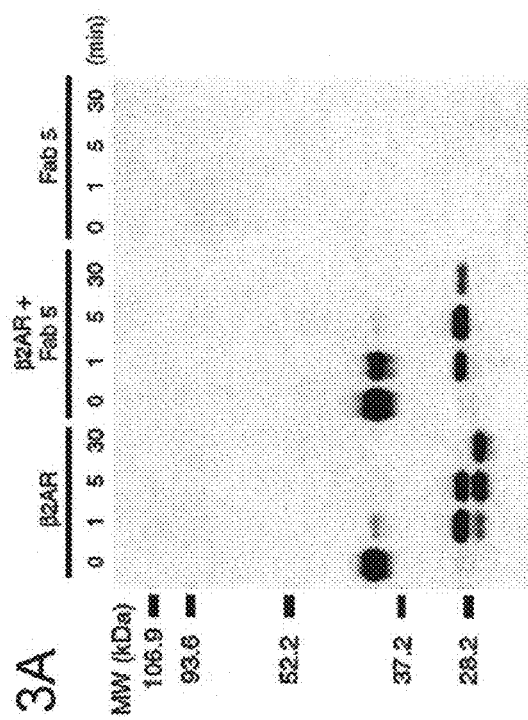
Figs. 3A and 3B

SEQUENCE LISTING

```
<160> NUMBER OF SEQ ID NOS: 3

<210> SEQ ID NO 1
<211> LENGTH: 214
<212> TYPE: PRT
<213> ORGANISM: mus musculis
<220> FEATURE:
<221> NAME/KEY: UNSURE
<222> LOCATION: (0)...(0)
<223> OTHER INFORMATION: Fab5 light chain

<400> SEQUENCE: 1

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ile Gly
    50                  55                  60

Thr Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 2
<211> LENGTH: 217
<212> TYPE: PRT
<213> ORGANISM: mus musculis
<220> FEATURE:
<221> NAME/KEY: UNSURE
<222> LOCATION: (0)...(0)
<223> OTHER INFORMATION: Fab 5 Heavy chain

<400> SEQUENCE: 2

Glu Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Ile Phe Thr Asp Tyr
```

-continued

```
              20                  25                  30
Tyr Ile Asn Trp Val Arg Gln Arg Thr Gly Gln Gly Phe Glu Trp Ile
            35                  40                  45

Gly Glu Ile Tyr Pro Gly Ser Gly Asn Ile Asp Tyr Asn Glu Arg Phe
        50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Val Arg Gly Phe Gly Tyr Trp Gly Gln Gly Thr Thr Leu Thr Val Ser
            100                 105                 110

Ser Ala Lys Thr Thr Pro Pro Ser Val Tyr Pro Leu Ala Pro Gly Ser
            115                 120                 125

Ala Ala Gln Thr Asn Ser Met Val Thr Leu Gly Cys Leu Val Lys Gly
        130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
            165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
            195                 200                 205

Lys Ile Val Pro Arg Asp Cys Gly Cys
    210                 215

<210> SEQ ID NO 3
<211> LENGTH: 10
<212> TYPE: PRT
<213> ORGANISM: homo sapien

<400> SEQUENCE: 3

Ile Asp Lys Ser Glu Gly Arg Phe His Val
1               5                   10
```

METHOD FOR OBTAINING G PROTEIN-COUPLED RECEPTOR (GPCR) DIFFRACTION-QUALITY CRYSTALS EMPLOYING A MONOCLONAL ANTIBODY THAT BINDS TO THE THIRD INTRACELLULAR LOOP (IL3)

GOVERNMENT RIGHTS

This work was supported in part by federal grant number NS28471 from the National Institutes of Health. The federal government has certain rights in this invention.

BACKGROUND

G protein-coupled receptor (GPCR) signaling plays a vital role in a number of physiological contexts including, but not limited to, metabolism, inflammation, neuronal function, and cardiovascular function. For instance, GPCRs include receptors for biogenic amines, e.g., dopamine, epinephrine, histamine, glutamate, acetylcholine, and serotonin; for purines such as ADP and ATP; for the vitamin niacin; for lipid mediators of inflammation such as prostaglandins, lipoxins, platelet activating factor, and leukotrienes; for peptide hormones such as calcitonin, follicle stimulating hormone, gonadotropin releasing hormone, ghrelin, motilin, neurokinin, and oxytocin; for non-hormone peptides such as beta-endorphin, dynorphin A, Leu-enkephalin, and Met-enkephalin; for the non-peptide hormone melatonin; for polypeptides such as C5a anaphylatoxin and chemokines; for proteases such as thrombin, trypsin, and factor Xa; and for sensory signal mediators, e.g., retinal photopigments and olfactory stimulatory molecules. GPCRs are of immense interest for drug development.

Efforts to crystallize GPCRs have been frustrated by intrinsic characteristics of integral membrane proteins. Bovine rhodopsin is the only GPCR for which a high-resolution structure has been determined by X-ray crystallography; and this is in part due to its natural abundance and atypical stability. The seven hydrophobic transmembrane helices of GPCRs make poor surfaces for crystal contacts, and the extracellular and intracellular domains are often relatively short and/or poorly structured.

SUMMARY OF THE INVENTION

An antibody that specifically binds a three dimensional epitope of the IC3 loop of a GPCR is provided. In certain embodiments, the antibody may specifically bind to the IC3 loop of the β2 adrenoreceptor. Also provided is a complex comprising a GPCR and a monovalent antibody that binds to a three dimensional epitope of the IC3 loop of that GPCR. The complex may be in a crystalline form.

A method is also provided. In general terms, the method comprises: a) contacting a GPCR with a monovalent antibody that specifically binds to a three dimensional epitope of the IC3 loop of a GPCR under binding conditions to form a complex; and b) crystallizing the complex. In one embodiment, the GPCR comprises the β2AR IC3 loop, and the Fab fragment may bind to the β2AR IC3 loop. The GPCR may also be a hybrid GPCR that contains the IC3 loop of β2AR.

Also provided is a method comprising reconstituting a GPCR in artificial phospholipid vesicles to make an antigen; and immunizing an animal with the antigen. The animal may be a rabbit, mouse or chicken, for example.

A method comprising screening a plurality of hybridoma lines obtained from an animal immunized with phospholipid vesicles comprising a GPCR for a hybridoma that produces an antibody that bind to a three dimensional epitope of the IC3 loop of said GPCR is also provided. This method may further comprise isolating a hybridoma line that produces the antibody.

A method of making GPCR-containing vesicular antigens is also provided, as is a method of screening hybridomas for the production of antibodies that bind to GPCR-containing vesicles.

A method of using the antibody as a treatment for a GPCR-mediated disorder is also provided.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 3A and 3B. Fab 5 binds IC3 (labeled as IL3) of the $\beta_2$AR but does not effect structural changes associated with G protein activation. 3A, Western blot analysis of the $\beta_2$AR digested with trypsin in the absence and presence of Fab 5. The fragmented $\beta_2$AR was visualized using an Alexa-680 labeled M1 antibody against the N-terminal Flag epitope. In the absence of Fab 5, two fragments at approximately 27 and 29 kDa appear corresponding to cleavage in the third intracellular loop. In contrast, the presence of Fab 5 protects the N-terminal end of the loop thus leaving the larger of the two fragments. The diagram shows the third intracellular loop connecting TM5 and TM6. The loop is marked with MW indicators corresponding to N-terminal fragments containing the Flag epitope. Residues sensitive to trypsin digest are shown in red. 3B, The change in the bimane fluorescence of $\beta_2$AR labeled with monobromobimane at H271C at the cytoplasmic end of TM6. Bimane fluorescence is quenched by W135 at the cytoplasmic end of TM3 upon agonist binding[9]. The response to the full agonist isoproterenol, isoproterenol plus Fab 5, and Fab 5 alone are shown. Fluorescence intensity was corrected for background fluorescence from buffer and ligands in all experiments. The data are the mean±S.E. of two independent experiments performed in triplicate.

DEFINITIONS

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with general dictionaries of many of the terms used in this disclosure. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Figure 1:
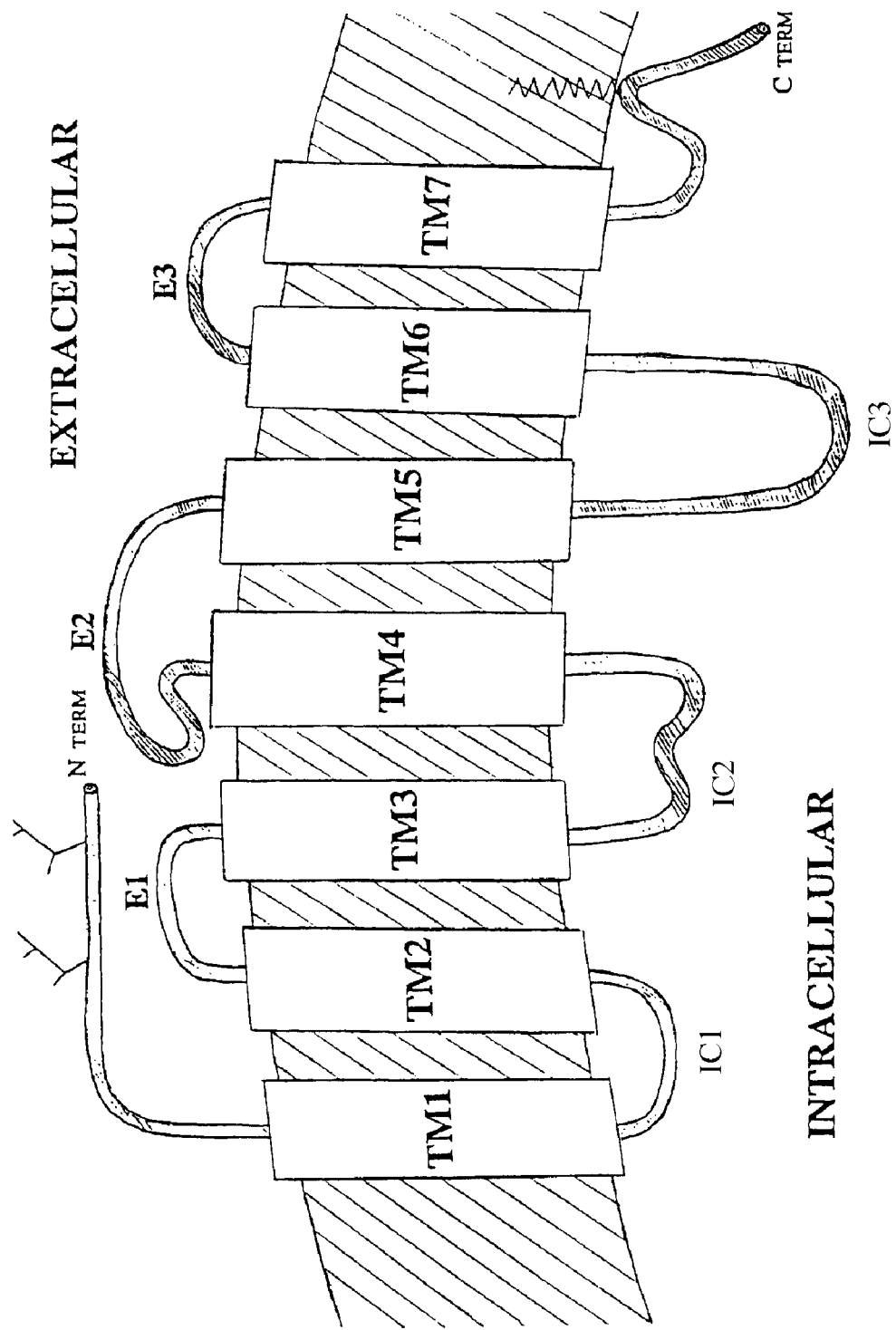
FIG. 1 is a schematic illustration of a GPCR, showing the canonical transmembrane regions (TM1, TM2, TM3, TM4, TM5, TM6, and TM7), intracellular regions (IC1, IC2, and IC3), and extracellular regions (EC1, EC2, and EC3).

"G-protein coupled receptors", or "GPCRs" are polypeptides that share a common structural motif, having seven regions of between 22 to 24 hydrophobic amino acids that form seven alpha helices, each of which spans a membrane. As illustrated in FIG. 1, each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. GPCR structure and classification is generally well known in the art, and further discussion of GPCRs may be found in Probst, DNA Cell Biol. 1992 11:1-20; Marchese et al Genomics 23: 609-618, 1994; and the following books: Jürgen Wess (Ed) Structure-Function Analysis of G Protein-Coupled Receptors published by Wiley-Liss (1st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). A schematic representation of an exemplary GPCR is shown in FIG. 1. A GPCR may be naturally occurring or non-naturally occurring (i.e., altered my man).

The term "naturally-occurring" in reference to a GPCR means a GPCR that is naturally produced (for example and not limitation, by a mammal or by a human). Such GPCRs are found in nature. The term "non-naturally occurring" in reference to a GPCR means a GPCR that is not naturally-occurring. Wild-type GPCRs that have been made constitutively active through mutation, and variants of naturally-occurring GPCRs are examples of non-naturally occurring GPCRs. Non-naturally occurring GPCR may have an amino acid sequence that is at least 80% identical to, e.g., at least 90% identical to, at least 95% identical to or at lest 99% identical to, a naturally-occurring GPCR.

The term "ligand" means a molecule that specifically binds to a GPCR. A ligand may be, for example a polypeptide, a lipid, a small molecule, an antibody. A "native ligand" is a ligand that is an endogenous, natural ligand for a native GPCR. A ligand may be a GPCR "antagonist", "agonist", "partial agonist" or "inverse agonist", or the like.

A "modulator" is a ligand that increases or decreases a GPCR intracellular response when it is in contact with, e.g., binds, to a GPCR that is expressed in a cell. This term includes agonists, including partial agonists and inverse agonists, and antagonists.

A "deletion" is defined as a change in either amino acid or nucleotide sequence in which one or more amino acid or nucleotide residues, respectively, are absent as compared to an amino acid sequence or nucleotide sequence of a parental GPCR polypeptide or nucleic acid. In the context of a GPCR or a fragment thereof, a deletion can involve deletion of about 2, about 5, about 10, up to about 20, up to about 30 or up to about 50 or more amino acids. A GPCR or a fragment thereof may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a parental GPCR. "Insertion" generally refers to addition to one or more amino acid residues within an amino acid sequence of a polypeptide, while "addition" can be an insertion or refer to amino acid residues added at an N- or C-terminus, or both termini. In the context of a GPCR or fragment thereof, an insertion or addition is usually of about 1, about 3, about 5, about 10, up to about 20, up to about 30 or up to about 50 or more amino acids. A GPCR or fragment thereof may contain more than one insertion.

A "substitution" results from the replacement of one or more amino acids or nucleotides by different amino acids or nucleotides, respectively as compared to an amino acid sequence or nucleotide sequence of a parental GPCR or a fragment thereof. It is understood that a GPCR or a fragment thereof may have conservative amino acid substitutions which have substantially no effect on GPCR activity. By conservative substitutions is intended combinations such as gly, ala; val, ile, leu; asp, glu; asn, gln; ser, thr; lys, arg; and phe, tyr.

The term "biologically active", with respect to a GPCR, refers to a GPCR having a biochemical function (e.g., a binding function, a signal transduction function, or an ability to change conformation as a result of ligand binding) of a naturally occurring GPCR.

As used herein, the terms "determining," "measuring," "assessing," and "assaying" are used interchangeably and include both quantitative and qualitative determinations. Reference to an "amount" of a GPCR in these contexts is not intended to require quantitative assessment, and may be either qualitative or quantitative, unless specifically indicated otherwise.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

The term "fusion protein" or grammatical equivalents thereof is meant a protein composed of a plurality of polypeptide components, that while typically unjoined in their native state, are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, $\beta$-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, at least 75% free, or at least 90% free from other components with which it is naturally associated.

A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Operably linked" refers to an arrangement of elements wherein the components so described are configured so as to perform their usual function. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to a host cell. Typically, "vector construct," "expression vector," and "gene transfer vector," mean any nucleic acid construct capable of directing the expression of a gene of interest and which can transfer gene sequences to host cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into a host cell. Thus, the term includes cloning and expression vehicles, as well as viral vectors.

A first polynucleotide is "derived from" or "corresponds to" a second polynucleotide if it has the same or substantially the same nucleotide sequence as a region of the second polynucleotide, its cDNA, complements thereof, or if it displays sequence identity as described above.

A first polypeptide is "derived from" or "corresponds to" a second polypeptide if it is (i) encoded by a first polynucleotide derived from a second polynucleotide, or (ii) displays sequence identity to the second polypeptides as described above.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')$_2$, and or other antibody fragments that retain specific binding to antigen.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),). This term also encompasses so-called "phage display" antibodies.

A "monovalent" antibody is an antibody that has a single antigen binding region. Fab fragments, scFv antibodies, and phage display antibodies are types of monovalent antibodies, although others are known. A "Fab" fragment of an antibody has a single binding region, and may be made by papain digestion of a full length monoclonal antibody. A single chain variable (or "scFv") fragment of an antibody is an antibody fragment containing the variable regions of the heavy and light chains of immunoglobulins, linked together with a short flexible linker.

A "hybridoma" is a cell that is a hybrid of a spleen cell or other antibody producing cell and an immortal cell (e.g., a myeloma cell). Hybridomas are both immortal and capable of producing the genetically coded antibody. Hybridomas and methodologies for making hybridomas may be found in U.S. Pat. No. 6,420,140 and Harlow, (*Antibodies: A Laboratory Manual*, First Edition (1988) Cold Spring Harbor, N.Y.) for example.

A "complex" between an antibody an antigen is characterized by a $K_D$ (dissociation constant) of less than $10^{-6}$ M, less than $10^{-7}$ M, less than $10^{-8}$ M, less than $10^{-9}$ M, or less than $10^{-9}$ M.

The "IC3 loop" of a GPCR is the intracellular loop that is between transmembrane region 5 (TM5) and transmembrane region 6 (TM6) of the GPCR. Such regions are readily identifiable by analysis of the primary amino acid sequence of a GPCR.

The terms "specifically binds" and "specific binding" refer to the ability of an antibody to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

An antibody that specifically binds to a "three dimensional" epitope or "conformational" epitope is an antibody that specifically binds to a tertiary (i.e., three dimensional) structure a folded protein. Such an antibody binds at much reduced (i.e., by a factor of at least 2, 5, 10, 50 or 100) affinity to the linear (i.e., unfolded, denatured) form of the protein. The structure to which such an antibody binds contains amino acids that are dis-contiguous in the protein. In other words, binding of such an antibody to a polypeptide is dependent upon the polypeptide being folded into a particular three dimensional conformation.

DETAILED DESCRIPTION OF EXEMPLARY EMBODIMENTS

As noted above, various compositions are provided, including an antibody that specifically binds to a three dimensional epitope of the IC3 loop of a GPCR, a complex containing a monovalent fragment of the antibody and a GPCR, and a crystal containing the complex. Various crystallization methods are also provided. In particular embodiments, the GPCR to be complexed with the antibody may contain the β2AR IC3 loop, and, in certain embodiments, may be a hybrid GPCR that contains the IC3 loop of β2AR. Methods of preparing an antigen, and screening for an antibody are also provided. These embodiments are described in greater detail below.

Antibodies

A monoclonal antibody that that specifically binds to a three dimensional epitope of the IC3 loop of a GPCR is provided. Such antibodies may be made, in general terms, by reconstituting an active GPCR in phospholipid vesicles, immunizing a suitable animal with the phospholipid vesicles, and screening antibody-producing cells of the animal (or hybridomas thereof) for the antibody.

A GPCR may be produced and purified using conventional methods that may employ expressing a recombinant form of the GPCR in a host cell, and purifying the GPCR using affinity chromatography and/or antibody-based methods. In particular embodiments, the bactulovirus/Sf-9 system may be employed for expression, although other expression systems (e.g., bacterial, yeast or mammalian cell systems) may also be used. Exemplary methods for expressing and purifying GCPRs are described in, for example, Kobilka (Anal Biochem 1995 231, 269-71), Eroglu et al (EMBO 2002 3: 491-

496), Chelikani et al (Protein Sci. 2006 15:1433-40) and the book "Identification and Expression of G Protein-Coupled Receptors" (Kevin R. Lynch (Editor), Wiley-Liss (March 1998)), among many others.

Likewise, methods for reconstituting an active GPCR in phospholipid vesicles are known, and are described in: Luca et al (Proc. Natl. Acad. Sci. 2003 100:10706-11); Mansoor et al (Proc. Natl. Acad. Sci. 2006 103: 3060-3065); Niu et al, (Biophys J. 2005 89: 1833-1840); Shimada et al (J. Biol. Chem. 2002 277:31774-80); and Eroglu et al, (Proc. Natl. Acad. Sci. 2003 100: 10219-10224), among others. In certain cases, the GPCR and phospholipids may be reconstituted at high density (e.g., 1 mg receptor per mg of phospholipid). In particular embodiments, the phospholipids vesicles may be tested to confirm that the GPCR is active. In many cases, a GPCR may be present in the phospholipid vesicle in both orientations (in the normal orientation, and in the "upside down" orientation in which the intracellular loops are on the outside of the vesicle).

Any suitable animal, e.g., a warm-blooded animal, in particular a mammal such as a rabbit, mouse, rat, camel, sheep, cow or pig or a bird such as a chicken or turkey, may be immunized with the reconstituted GPCR using any of the techniques well known in the art suitable for generating an immune response. Procedures for immunizing animals are well known in the art, and are described in Harlow (*Antibodies: A Laboratory Manual*, First Edition (1988) Cold Spring Harbor, N.Y.) and Weir (*Handbook of Experimental Immunology* Vol 4, Blackwell Scientific Publishers, Oxford, England, 1986). As will be appreciated by one of ordinary skill in the art, the immunogen may be admixed with an adjuvant or hapten in order to increase the immune response (for example, complete or incomplete Freund's or lipid A adjuvant), or with a carrier such as keyhole limpet hemocyanin (KLH).

Once a suitable animal has been immunized and an immune response against the antigen has been established by the animal, antibody producing cells from the animal are screened to identify cells that produce antibodies having a desired activity. In many embodiments, these methods may employ hybridoma technology in which cells from the spleen of the immunized animal are fused with a suitable immortal cell to produce hybridoma cells. Supernatants from these hybridoma cells may be screened, and positive clones are expanded according to standard procedures (Harlow et al. *Antibodies: A Laboratory Manual*, First Edition (1988) Cold spring Harbor, N.Y.; and Spieker-Polet et al., supra).

The antibodies may be screened for binding to the GPCR folded into a native conformation by, e.g., cell staining to identify those antibodies that bind a three dimensional epitope in the GPCR. In certain cases, the antibodies may also be screened for binding to denatured GPCR. Antibodies that bind to the IC3 loop of the polypeptide may be identified using any of a variety of different means, depending on the GPCR. For example, the antibody can be tested to determine if it can block interactions with a G-protein, or it can be tested on a GPCR containing amino acid substitutions in the IC3 loop. Other methods are described in the examples section of this disclosure.

In alternative embodiments, a phage display antibody may be employed, methods for the production of which are well known (see, e.g., Scott et al. Science 1990 249: 386; Devlin et al., Science 1990 249: 404; U.S. Pat. Nos. 5,223,409, 5,733, 731, 5,498,530, 5,432,018, 5,338,665, and 5,922,545, for example).

Any known GPCR is suitable for use in the subject methods. A disclosure of the sequences and phylogenetic relationships between 277 GPCRs is provided in Joost et al. (Genome Biol. 2002 3:RESEARCH0063, the entire contents of which is incorporated by reference) and, as such, at least 277 GPCRs are suitable for the subject methods. A more recent disclosure of the sequences and phylogenetic relationships between 367 human and 392 mouse GPCRs is provided in Vassilatis et al. (Proc Natl Acad Sci 2003 100:4903-8 and www.primalinc.com, each of which is hereby incorporated by reference in its entirety) and, as such, at least 367 human and at least 392 mouse GPCRs are suitable for the subject methods. GPCR families are also described in Fredriksson et al (Mol. Pharmacol. 2003 63, 1256-72). Since the amino acid sequences of many GPCRs are available and their code sequences are known, the subject antibody may be made for any GPCR. For example, a human, mouse, rat, insect or plant GPCR may be used in the subject method.

The methods may be used, by way of exemplification, for purinergic receptors, vitamin receptors, lipid receptors, peptide hormone receptors, non-hormone peptide receptors, non-peptide hormone receptors, polypeptide receptors, protease receptors, receptors for sensory signal mediator, and biogenic amine receptors not including β2-adrenergic receptor. In certain embodiments, said biogenic amine receptor does not include an adrenoreceptor. α-type adrenoreceptors (e.g. $\alpha_{1A}$, $\alpha_{1B}$ or $\alpha_{1C}$ adrenoreceptors) and β-type adrenoreceptors (e.g. $\beta_1$, $\beta_2$, or $\beta_3$ adrenoreceptors) are discussed in Singh et al., J. Cell Phys. 189:257-265, 2001.

It is recognized that both naturally occurring and altered native (non-naturally occurring) GPCRs may be used in the subject methods. In certain embodiments, therefore, an altered native GPCR (e.g. a native GPCR that is altered by an amino acid substitution, deletion and/or insertion) such that it binds the same ligand as a corresponding native GPCR may be used in the subject methods.

As such, the following GPCRs (native or altered) find particular use as parental GPCRs in the subject methods: cholinergic receptor, muscarinic 3; melanin-concentrating hormone receptor 2; cholinergic receptor, muscarinic 4; niacin receptor; histamine 4 receptor; ghrelin receptor; CXCR3 chemokine receptor; motilin receptor; 5-hydroxytryptamine (serotonin) receptor 2A; 5-hydroxytryptamine (serotonin) receptor 2B; 5-hydroxytryptamine (serotonin) receptor 2C; dopamine receptor D3; dopamine receptor D4; dopamine receptor D1; histamine receptor H2; histamine receptor H3; galanin receptor 1; neuropeptide Y receptor Y1; angiotensin II receptor 1; neurotensin receptor 1; melanocortin 4 receptor; glucagon-like peptide 1 receptor; adenosine A1 receptor; cannabinoid receptor 1; and melanin-concentrating hormone receptor 1.

In certain embodiments, the antibody is a monovalent antibody that contains a single antigen binding region comprising variable heavy and variable light domains. Such antibodies, including Fab antibodies and scFv antibodies, may be produced from a monoclonal antibody after it is identified. In one embodiment, the monovalent antibody is an antibody containing the heavy and light variable regions from antibody 5, which is described in the examples section of this disclosure. Such antibodies include Fab fragment of antibody 5 (i.e., the Fab5 antibody) or a scFv antibody comprising the same variable domains as the Fab5 antibody, where the heavy and light variable domains of the Fab5 antibody have the following amino acid sequence:

Fab5 Light Chain:
(SEQ ID NO: 1)
DIKMTQSPSSMYASLGERVTITCKASQDINSYLSWFQQKPGKSPKTLIYR

ANRLVDGVPSRFIGTGSGQDYSLTISSLDYEDMGIYYCLQYDEFPYTFGG

-continued

```
GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC

Fab 5 Heavy chain:
                                         (SEQ ID NO: 2)
EVQLQQSGAELARPGASVKLSCKASGYIFTDYYINWVRQRTGQGFEWIGE

IYPGSGNIDYNERFKDKATLTADKSSTAYMQLSSLTSEDSAVYFCVRGF

GYWGQGTTLTVSSAKTTPPSVYPLAPGSAAQTNSMVTLGCLVKGYFPEPV

TVTWNSGSLSSGVHTFPAVLQSDLYTLSSSVTVPSSTWPSETVTCNVAHP

ASSTKVDKKIVPRDCGC
```

In certain cases, a subject antibody may contain: a) a heavy chain containing the CDR1, CDR2 and CDR3 regions of the heavy chain of an above-described antibody, separated by framework sequence and b) a light chain containing the CDR1, CDR2 and CDR3 regions of the light chain of that antibody, separated by framework sequence.

Also provided is a complex containing the GPCR and a single antigen binding region of the antibody. Such a complex may be formed under antibody binding conditions described in Harlow and Weir, supra. A crystal of the complex is also provided, and methods of making of which are described in greater detail below.

Crystallization Methods

A crystallization method is also provided. The method includes contacting a GPCR with a monovalent antibody that specifically binds to a three dimensional epitope of the IC3 loop of a GPCR under binding conditions to form a complex; and crystallizing the complex.

A subject complex may be crystallized using any of a variety of crystallization methods, many of which are reviewed in Caffrey *Membrane protein crystallization*. J Struct. Biol. 2003 142:108-32. In general terms, the methods are lipid-based methods that include adding lipid to the fusion protein prior to crystallization. Such methods have previously been used to crystallize other membrane proteins. Many of these methods including the exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al, *Lipidic cubic phases: a novel concept for the crystallization of membrane proteins*. Proc. Natl. Acad. Sci. 1996 93:14532-5; Gouaux, It's not just a phase: crystallization and X-ray structure determination of bacteriorhodopsin in lipidic cubic phases. Structure. 1998 6:5-10; Rummel et al, *Lipidic Cubic Phases: New Matrices for the Three-Dimensional Crystallization of Membrane Proteins*. J. Struct. Biol. 1998 121:82-91; and Nollert et al *Lipidic cubic phases as matrices for membrane protein crystallization* Methods. 2004 34:348-53, which publications are incorporated by reference for disclosure of those methods. Bicelle crystallization methods are described in, for example: Faham et al *Crystallization of bacteriorhodopsin from bicelle formulations at room temperature*. Protein Sci. 2005 14:836-40. 2005 and Faham et al, *Bicelle crystallization: a new method for crystallizing membrane proteins yields a monomeric bacteriorhodopsin structure*. J Mol Biol. 2002 Feb. 8; 316(1):1-6, each of which are incorporated by reference for disclosure of those methods.

Also provided is a method of determining a crystal structure. This method may comprise receiving an above described complex, crystallizing the complex to produce a crystal, and obtaining atomic coordinates of the GPCR from the crystal. The complex may be received from a remote location (e.g., a different laboratory in the same building or campus, or from a different campus or city), and, in certain embodiments, the method may also comprise transmitting the atomic coordinates, e.g., by mail, e-mail or, using the internet, to the remote location or to a third party.

In other embodiments, the method may comprise forwarding a complex to a remote location, where the complex may be crystallized and analyzed, and receiving the atomic coordinates of the GPCR.

In certain cases, the GPCR to be crystallized may be a GPCR that has been modified to contain a three dimensional epitope from the IC3 loop from a different GPCR (e.g., the β2 GPCR). In these embodiments, once a suitable antibody has been identified for a first GPCR, the antigen binding region for that antibody can be swapped from the first GPCR into a second GPCR to make a chimeric GPCR. The chimeric GPCR can then be bound to a monovalent antibody, and crystallized using a method described herein. In one embodiment, the entire IC3 loop, including the three dimensional epitope contained in the loop, may be grafted from one GPCR to another to produce an active GPCR. Such methods have been successfully performed by others, e.g., Kim et al (Biochemistry 2005 44:2284-92); Yamashita et al (J. Biol. Chem. 2000 275:34272-9); Geiser et al (Protein Sci. 2006 15:1679-90); Tumova et al (J. Biol. Chem. 2003 278:8146-53); Wong et al (J. Biol. Chem. 1990 265:6219-24) and Wess et al (FEBS Lett. 1989 258:133-6).

The IC3 region of a GPCR lies in between transmembrane regions TM5 and TM6 and, may be about 12 amino acids (CXCR3 and GPR40) to about 235 amino acids (cholinergic receptor, muscarinic 3) in length, for example. The TM5, IC3, and TM6 regions are readily discernable by one of skill in the art using, for example, a program for identifying transmembrane regions; once transmembrane regions TM5 and TM6 regions are identified, the IC3 region will be apparent. The TM5, IC3, and TM6 regions may also be identified using such methods as pairwise or multiple sequence alignment (e.g. using the GAP or BESTFIT of the University of Wisconsin's GCG program, or CLUSTAL alignment programs, Higgins et al., Gene. 1988 73:237-44), using a target GPCR and, for example, GPCRs of known structure.

Suitable programs for identifying transmembrane regions include those described by Moller et al., (Bioinformatics, 17:646-653, 2001). A particularly suitable program is called "TMHMM" Krogh et al., (Journal of Molecular Biology, 305:567-580, 2001). To use these programs via a user interface, a sequence corresponding to a GPCR or a fragment thereof is entered into the user interface and the program run. Such programs are currently available over the world wide web, for example at the website of the Center for Biological Sequence Analysis at cbs.dtu.dk/services/. The output of these programs may be variable in terms its format, however they usually indicate transmembrane regions of a GPCR using amino acid coordinates of a GPCR.

When TM regions of a GPCR polypeptide are determined using TMHMM, the prototypical GPCR profile is usually obtained: an N-terminus that is extracellular, followed by a segment comprising seven TM regions, and further followed by a C-terminus that is intracellular. TM numbering for this prototypical GPCR profile begins with the most N-terminally disposed TM region (TM1) and concludes with the most C-terminally disposed TM region (TM7).

Accordingly, in certain embodiments, the amino acid coordinates of the TM5, IC-3, and TM6 regions of a GPCR are identified by a suitable method such as TMHMM.

In certain cases, once the TM5-IC3-TM6 segment is identified for a GPCR, a suitable region of amino acids is chosen for substitution with the amino acid sequence of an IC3 region of another GPCR, e.g. the β2 GPCR. In certain embodiments, the substituted region may be identified using conserved or semi-conserved amino acids in the TM5 and TM6 transmembrane regions.

For GPCRs that contain no conserved proline residues in TM5 and TM6, positions for inserting a different IC3 loop may be based on two considerations: a) alignment of the sequence of the GPCR with receptor members of the same subfamily (which contained conserved proline residues in TM5 or TM6; b) by identifying the juxtaposition to the TM5/TM6 regions by hydrophobicity analysis.

In addition to substituting IC3 region of a GPCR with a stable, folded protein insertion, as described above, in certain cases, the C-terminal region of the GPCR (which is C-terminal to the cysteine palmitoylation site that is approximately 10 to 25 amino acid residues downstream of a conserved NPXXY motif), may be deleted. In certain cases, the 20-30 amino acids immediately C-terminal to the cysteine palmitoylation site are not deleted.

In one embodiment, a region containing the binding region of antibody 5 described below (i.e., a region containing nine amino acids at the amino-terminal end of the β2AR IC3 loop (I233-V242), having the amino acid sequence IDKSEGRFHV; SEQ ID NO:3 and also containing L266 and/or K270 from the C-terminal end of the β2AR IC3 loop) may be substituted into a different (non-β2AR) GPCR at the same position, to produce a chimeric GPCR. That chimeric GPCR may be complexed with a monovalent version of antibody 5 (e.g., a Fab fragment of antibody 5 or a scFv antibody) to make a complex that can be crystallized. In certain embodiments, the antibody 5 binding site sequences may be transferred along with amino acids that flank the binding site (e.g., up to 2, 3, 4, or 5 amino acids from each side). In particular embodiments, the entire IC3 region of the non-β2AR GPCR may be substituted with the IC3 region of β2AR. In certain cases, the transferred may contain I233 to K270 of β2AR GPCR, and may contain amino acids that flank that sequence (e.g., up to 2, 3, 4, or 5 amino acids from each side). In other cases, two regions may be transferred, one containing the amino acid sequence of I233 to V242, and the other containing the amino acid sequence of L266 to K270. These sequences can be transferred to the N-terminus and the C-terminus of the recipient GPCR's IC3, respectively.

Thus, a chimeric GPCR used in the method may contain a) an IC3 loop of one GPCR (e.g., the β2 GPCR), and b) TM1-TM7, IC1 and IC2 regions of another GPCR.

Methods of Treatment

Certain of the above-described antibodies may have therapeutic utility and may be administered to a subject having a condition in order to treat the subject for the condition. The therapeutic utility for an antibody may be determined by the GPCR to which the antibody binds in that signaling via that GPCR is linked to the condition. In certain cases, the GPCR may be activated in the condition via by binding by a ligand. In other embodiments, the GPCR may be mutated to make it constitutively active, for example. A subject antibody may be employed for the treatment of a GPCR-mediated condition such as schizophrenia, migraine headache, reflux, asthma, bronchospasm, prostatic hypertrophy, ulcers, epilepsy, angina, allergy, rhinitis, cancer e.g. prostate cancer, glaucoma and stroke. Further exemplary GPCR-related conditions at the On-line Mendelian Inheritance in Man database found at the world wide website of the NCBI.

In certain embodiments as noted above, the antibody may bind to the β2-adrenoreceptor, in which case it may be employed in the treatment of a condition requiring relaxation of smooth muscle of the uterus or vascular system. Such an antibody may be thus used for the prevention or alleviation of premature labour pains in pregnancy, or in the treatment of chronic or acute asthma, urticaria, psoriasis, rhinitis, allergic conjunctivitis, actinitis, hay fever, or mastocytosis, which conditions have been linked to the β2-adrenoreceptor. In these embodiments, the antibody may be employed as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A subject antibody may be mixed with the other drug substance in a fixed pharmaceutical composition or it may be administered separately, before, simultaneously with or after the other drug substance. Such anti-inflammatory drugs include steroids, in particular glucocorticosteroids such as budesonide, beclamethasone, fluticasone, ciclesonide or mometasone or steroids described in WO 0200679 especially those of Examples 3, 11, 14, 17, 19, 26, 34, 37, 39, 51, 60, 67, 72, 73, 90, 99 and 101, LTB4 antagonists such as those described in U.S. Pat. No. 5,451,700, LTD4 antagonists such as montelukast and zafirlukast, and PDE4 inhibitors such as Ariflo® (GlaxoSmith Kline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene) and KW-4490 (Kyowa Hakko Kogyo) and A2a agonists such as those described in EP 1052264, EP 1241176, WO 0023457, WO0077018, WO 0123399, WO 0160835, WO 0194368, WO 0200676, WO 0222630, WO 0296462, WO 0127130, WO 0127131, WO 9602543, WO 9602553, WO 9828319, WO 9924449, WO 9924450, WO 9924451, WO 9938877, WO 9941267, WO 9967263, WO 9967264, WO 9967265, WO 9967266, WO 9417090, EP 409595A2 and WO 0078774 and A2b antagonists such as those described in WO 02/42298. Such bronchodilatory drugs include anticholinergic or antimuscarinic agents, in particular ipratropium bromide, oxitropium bromide and tiotropium bromide. In general terms, these protocols involve administering to an individual suffering from a GPCR-related disorder an effective amount of an antibody that modulates a GPCR to modulate the GPCR in the host and treat the individual for the disorder.

In some embodiments, where a reduction in activity of a certain GPCR is desired, one or more compounds that decrease the activity of the GPCR may be administered, whereas when an increase in activity of a certain GPCR is desired, one or more compounds that increase the activity of the GPCR activity may be administered.

A variety of individuals are treatable according to the subject methods. Generally such individuals are mammals or mammalian, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans. Subject treatment methods are typically performed on individuals with such disorders or on individuals with a desire to avoid contracting such disorders.

A variety of publications describe treatment regimens using the antibodies including, for example, published patent applications 20080159981, 20080102069, 20070142346, 20060018899, 20050148607 and 20030228663, as well as U.S. Pat. Nos. 7,306,801, 6,399,063, 6,387,371 and 6,165, 464, which are each incorporated by reference in their entirety. In general terms, these documents described methods including administering a therapeutic monoclonal antibody to a subject, singly or in combination with another agent. The subject may then be monitored for a clinically beneficial response, where a beneficial response to the antibody can be assessed according to whether an individual patient experiences a desirable change in disease status.

In particular embodiments, the antibody may have a translocation sequence (e.g., an HIV TAT, AntP, or VP22 traslocation sequence, or other short sequence rich in basic amino acids) which facilitates translocation of the antibody across the plasma membrane into the cytoplasm of a target cell. Such translocation sequences and their use are known and reviewed in, for example, Gupta (Drug Deliv. Rev. 2005 57:637-51), Steffen (Methods Mol. Biol. 2001 161:141-8) and Hansen (Scientific World Journal. 2005 5:782-8).

In order to further illustrate the present invention, the following specific examples are given with the understanding that they are being offered to illustrate the present invention and should not be construed in any way as limiting its scope.

EXAMPLE 1

Antigen Production

Antigen was prepared by reconstituting purified, functional $\beta_2AR$ at high density into phospholipid vesicles (1 mg receptor per mg of phospholipids) using the following method.

$\beta_2AR$ having an amino terminal Flag epitope tag and a carboxyl hexahistidine tag was expressed in Sf9 insects cells and purified by sequential M1 antibody and alprenolol affinity chromatography as previously described (Kobilka *Anal Biochem* 1995 231, 269-71). Purified $\beta_2AR$ was immobilized on a Ni column and equilibrated with 10 column volumes of a mixture of 5 mg/ml DOPC (Avanti Polar Lipids) and 0.5 mg/ml Lipid A (Sigma) in 1% (w/v) octylglucoside (Anatrace), 100 mM NaCl, 20 mM Hepes pH 7.5 and 1 µM carazolol (a $\beta_2AR$ antagonist). The $\beta_2AR$ was then eluted in the same buffer containing 200 mM imidazole. The concentration of the eluted $\beta_2AR$ was adjusted to 5 mg/ml. This usually involved diluting the protein with the same buffer, but occasionally required concentrating the protein up to twofold with an Amicon ultrafiltration cell (100 kDa pore). The protein was then dialyzed against phosphate buffered saline containing 1 µM carazolol at 4° C. to remove detergent. The reconstituted protein was stored at −80° C. prior to use for immunization.

The phospholipid environment ensures the functional integrity of the protein after injection into mice. To provide additional stability, the $\beta_2AR$ was liganded with carazolol, a high affinity inverse agonist. To facilitate the immune response, phospholipid vesicles consisted of a 10:1 mixture (by weight) of DOPC and the adjuvant Lipid A. The generated vesicles contained randomly oriented $\beta_2AR$, so that both cytoplasmic and extracellular domains are presented to immune cells.

EXAMPLE 2

Antibody Production

Monoclonal antibodies (MABs) were generated using a conventional fusion protocol, as follows:
Myeloma Cell Lines
The P3x63Ag8.653 myeloma cell line (ATCC # CRL-1580; Lot No. 1131010) was used for the fusion experiment performed with splenocytes from immunized mice.

Cell Culture
Myeloma cells were propagated in Dulbecco's Modified Eagle's Medium (DMEM-high glucose) supplemented with 10% Fetal Bovine Serum (FBS), 0.15 g/L oxaloacetate, 0.05 g/L pyruvate, 0.0082 g/L bovine insulin (OPI supplement), 10% NCTC109 medium and 4 mM L-glutamine. This formulation is referred to the SDMEM formulation. Newly formed hybridoma were selected in SDMEM supplemented with HAT mixture ($1.0\times10^{-4}$ M Hypoxanthine, $4.0\times10^{-6}$ M Aminopterin, $1.6\times10^{-5}$ M thymidine), 5% hybridoma cloning factor, gentamicin (50 µg/ml) and β-mercaptoethanol at 0.055 mM. This formulation is referred as SDMEM-HAT. After selection, the newly formed hybridomas were propagated in SDMEM supplemented with 2% hybridoma cloning factor HT mixture ($1.0\times10^{-4}$ M hypoxanthine, $1.6\times10^{-5}$ M thymidine). This formulation is referred as DMEM-HT. For in vitro antibody production, the hybridomas were propagated in SDMEM supplemented with 1% hybridoma cloning factor and 5-10% low-IgG FBS.
Cell Fusion Protocol Balb/c mice were immunized weekly with 30 µg of $\beta_2AR$ in liposomes. The mice were injected intraperitoneally with 15 µg of antigen and subcutaneously at 2 sites with 7.5 mg of antigen. Final boosts of 10 µg of $\beta_2AR$ were given intraperitoneally and intravenously on day 3 and 4 before fusion. Spleens were harvested aseptically, placed in cold DMEM, diced and homogenized. The homogenate was centrifuged at 1000 rpm for 5 minutes. The cell pellet was incubated with 5 ml of Red cell lysis buffer (Sigma R7757) for 3-5 mins. DMEM (20 ml) was added and the cells were centrifuged at 1000 rpm for 5 minutes. The pellet was rinsed twice in 20 ml DMEM. The final pellet was resuspended in 30 mL DMEM. Spleen and myeloma cells were combined at a 3:1 ratio, centrifuged (1000 rpm) and resuspend in DMEM. The centrifugation was repeated and 1 mL PEG-1500 (50% solution) was added to the cell pellet over 3 min with gentle mixing. 4 mL of SDMEM was slowly added to cells over 2 min. After 1 min incubation, 20 mL of SDMEM was added over 1 min. The suspension was centrifuge (1000 rpm) and the pellet was resuspended in a total of 30 mL HAT-SDMEM and incubate at 37° C. for 2 hours. HAT-SDMEM media was added to achieve a cell density of $5\times10^4$ cells/well and dispensed into 96-well plates at 200 µL per well. Cells were incubated for 11 days before screening media for antibody production.

Figure 4:
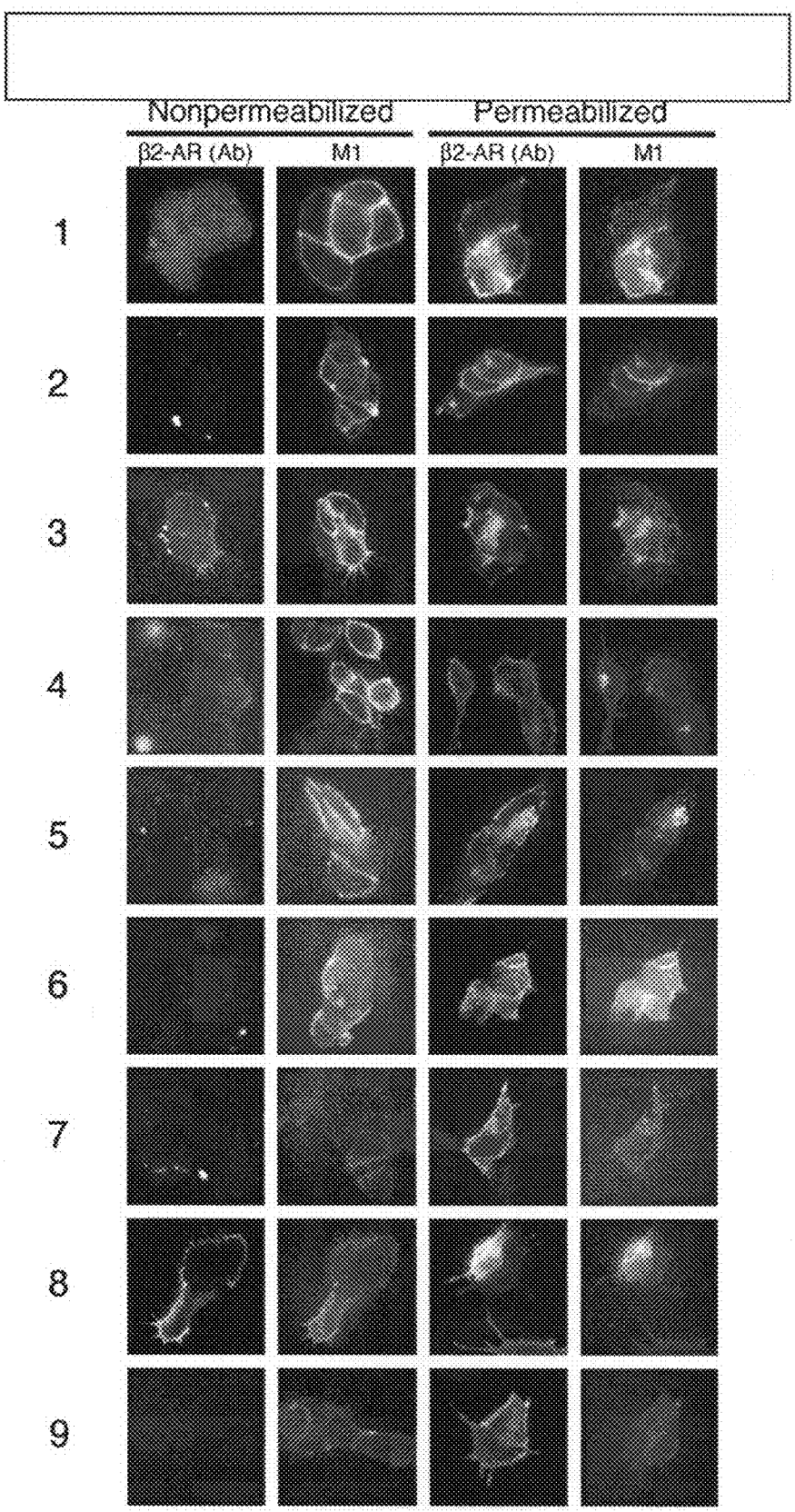
FIG. 4 Fluorescence images showing monoclonal antibody detection of flag tagged β$_2$AR stably expressed in HEK-293 cells. HEK-293 cells stably expressing a flag tagged version of the β$_2$AR were cultured on coverslips and processed for immunocytochemistry. After fixation, with 4% paraformaldehyde, the cells were washed and blocked with 2.5% goat serum in PBS alone (nonpermeabilized) or with 0.5% NP-40 in PBS (permeabilized). The cells were incubated with the β$_2$AR specific antibody indicated on the left side of the figure. After several washes, the β$_2$AR monoclonal antibodies were detected with a Texas Red conjugated anti-mouse secondary antibody. To demonstrate that all of the cells are expressing the receptor they were subsequently stained with an Alexa-488 conjugated M1 antibody (M1 column), which recognizes the amino terminal flag tag on the β$_2$AR. Antibodies 1, 3, 4 and 8 stain cells in the absence of permeabilization and therefore bind an epitope on the extracellular face of the receptor. In contrast, antibodies 2, 5, 6, 7 and 9 only stain cells that have been permeabilized indicative of an intracellular epitope. The images shown are representative of at least 3 experiments. All images were acquired using an Axioplan 2 microscope (Carl Zeiss MicroImaging), fitted with a camera (RTE/CCD-1300-Y/HS; Roper Scientific) controlled using IPLab software (BD Bioscience).

Fusions from two mice yielded seventeen hybridoma clones that produced antibody against $\beta_2AR$ as determined by an ELISA assay on immobilized phospholipid vesicles containing purified $\beta_2AR$. Nine of these hybridomas produced sufficient quantities of $\beta_2AR$-specific antibody for further characterization. The antibodies were characterized as binding the intracellular or extracellular surface of the receptor in immunofluorescence experiments with HEK-293 cells stably expressing an N-terminally FLAG-tagged version of the $\beta_2AR$. Antibodies that recognize an intracellular epitope only stain permeabilized cells. Staining of cells that were either fixed or fixed and permeabilized indicated that five of the antibodies bound to the intracellular face and four bound to the extracellular surface (FIG. 4).

EXAMPLE 3

Antibody Screening

Figures 2A, 2B:
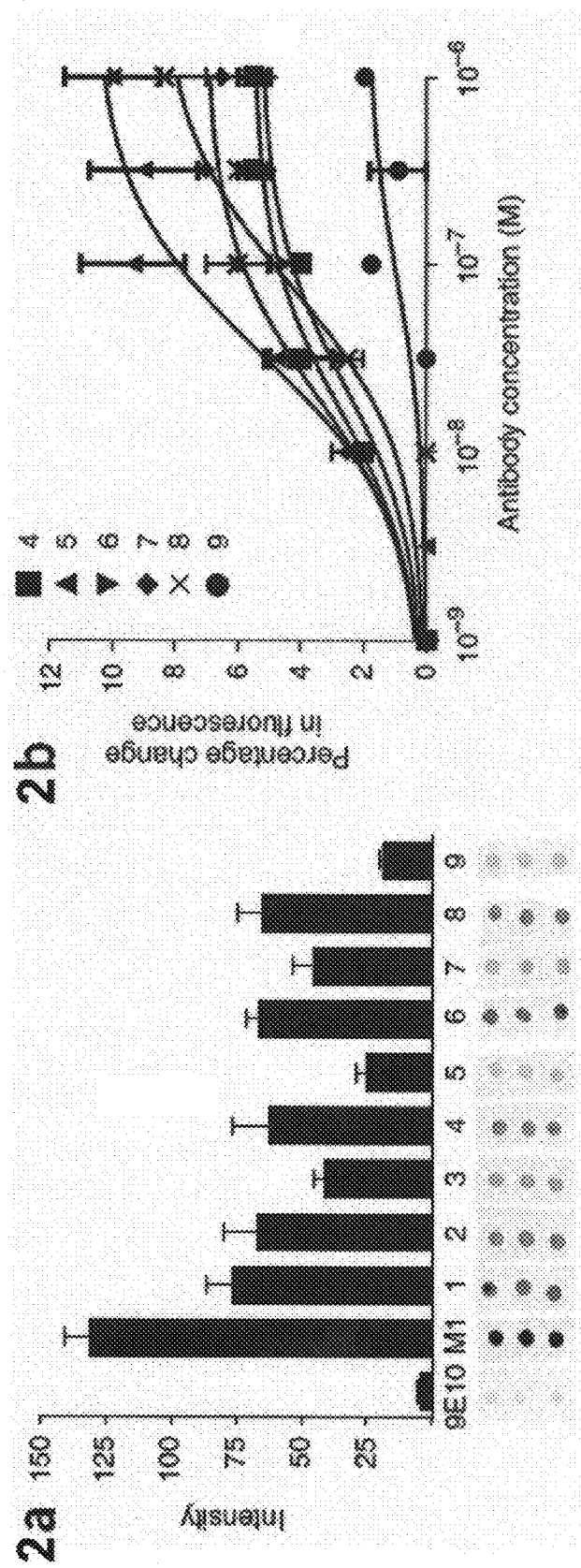
FIGS. 2A and 2B. Binding characteristics of $\beta_2$AR-specific antibodies. 2A, Dot-blots showing binding of nine $\beta_2$AR specific antibodies to denatured receptor. Equal amounts of $\beta_2$AR denatured with SDS and β-mercaptoethanol were spotted in triplicate on nitrocellulose strips. The strips were blocked with 5% non-fat dry milk in PBS-Tween (0.05% Tween-20) and then probed with 1 mg/ml of the indicated antibodies diluted in blocking buffer. Binding of the primary antibody to the denatured $\beta_2$AR was detected with an Alexa-688 labeled anti-mouse secondary antibody. The top panel is a graphical representation of the average dot intensity from three independent experiments. The lower panel is a representative experiment. The binding of all 9 antibodies to denatured $\beta_2$AR is reduced compared to M1 binding to the linear Flag epitope. 2B, Dose-response curves showing the effect on increasing amounts of antibodies 4-9 on the fluorescence of $\beta_2$AR labeled at C265 with tetramethylrhodamine ($\beta_2$AR-TMR). $\beta_2$AR-TMR was diluted to 4 nM in 500 μL of buffer consisting of 0.1% dodecylmaltoside, 100 mM sodium chloride, and 20 mM HEPES buffer (pH 7.5). Data represent an n of 3.

Antibodies were screened for binding to a three dimensional epitope on the three-dimensional surface on the IC3 of the native $\beta_2AR$, rather than a flexible linear epitope. Nine MABs were screened, along with positive (M1 antibody) and negative (9E10) controls, for binding to $\beta_2AR$ denatured with sodium dodecyl sulfate (SDS) and spotted on nitrocellulose (FIG. 2A). Antibody 5 and antibody 9 showed the weakest binding to denatured protein, even though they showed immunostaining comparable to M1 on binding to native receptor in fixed cells (see FIG. 4). The reduced binding of antibody 5 and antibody 9 to SDS denatured $\beta_2AR$ showed that these antibodies bind to a three-dimensional epitope.

Antibodies 2, 5, 6, 7 and 9 all reacted with intracellular epitopes. To select for antibodies that may interact with IC3, we examined the effect of antibody binding on the fluorescence of $\beta_2AR$ labeled at C265 (at the cytoplasmic end of TM6) with tetramethylrhodamine. Tetramethylrhodamine bound to C265 is predicted to lie at the interface between TM5 and TM6. Previous studies have shown that tetramethylrhodamine binding to C265 is sensitive to ligand-induced three dimensional changes in the $\beta_2AR$ (Swaminath et al, J. Biol. Chem. 2004 279: 686-691). As such, antibodies binding to IC3 may stabilize a specific conformation of TM5 relative to TM6 that would be detected by a change in tetramethylrhodamine fluorescence. It can be seen that antibody 5 induced the largest fluorescence response and had the highest affinity for the $\beta_2AR$ (FIG. 2B). The fluorescence change induced by antibody 5 was significantly greater than the response to antibody 9, the other intracellular binder that reacted weakly to SDS denatured receptor. It is notable that there was a response to antibody 8 and antibody 4, two antibodies that bind to an extracellular epitope. This suggests that binding of these antibodies to the extracellular surface of the $\beta_2AR$ influences the structure around the cytoplasmic end of TM6.

Based on the results of assays shown in FIGS. 2A and 2B antibody 5 was chosen for crystallography experiments. Antibody 5 bound to an intracellular epitope, it exhibited relatively high affinity for native $\beta_2AR$ (FIG. 2B), but bound weakly to SDS denatured protein (FIG. 2A). Antibody 5 also induced the largest fluorescence response in $\beta_2AR$ labeled at C265 with tetramethylrhodamine. Based on these experiments, antibody 5 binds to a three dimensional epitope on the native third intracellular loop.

EXAMPLE 4

Antibody Characterization

Figure 5:
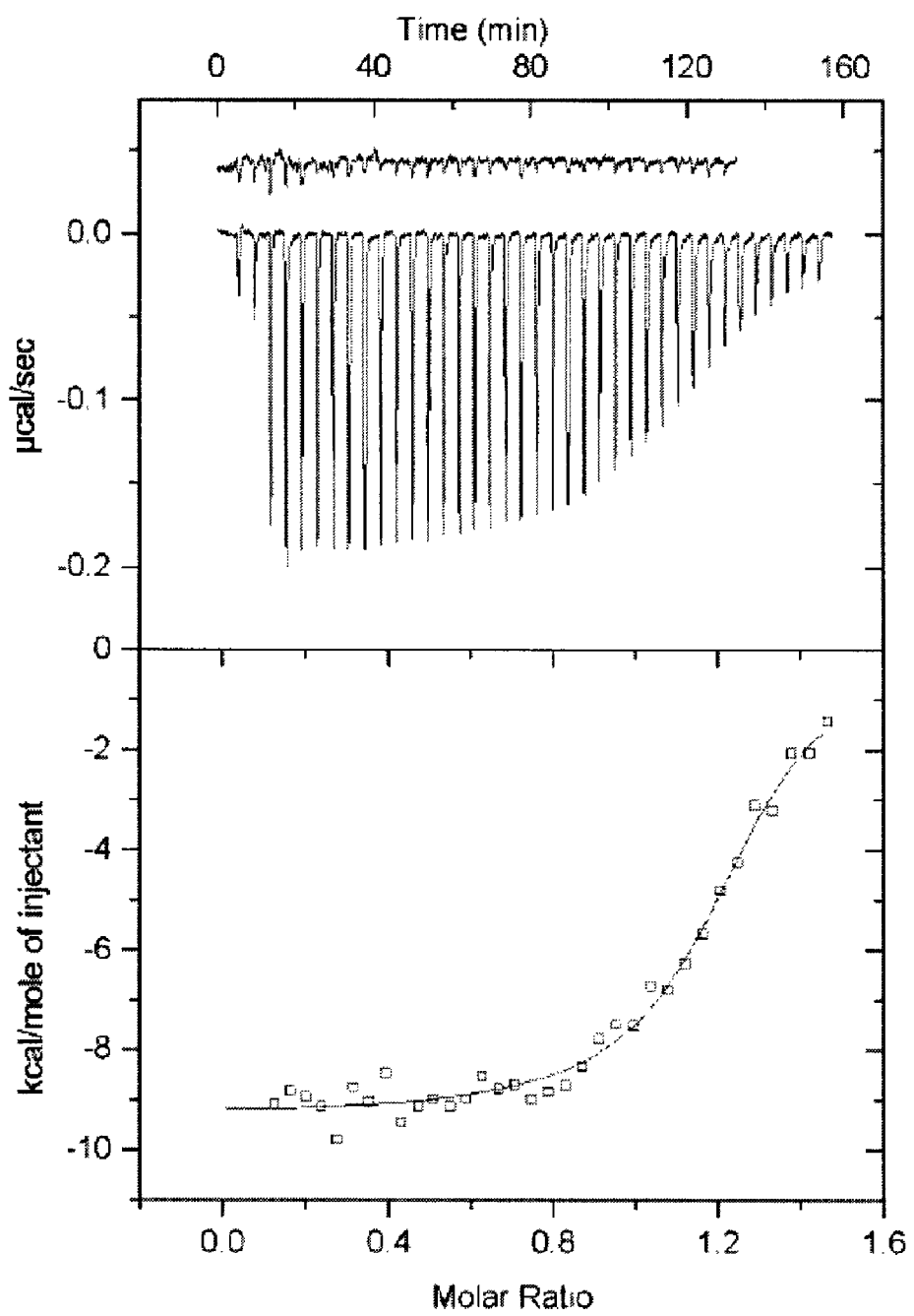
FIG. 5 Affinity of Fab 5 for purified β$_2$AR determined by isothermal titration calorimetry (ITC). ITC measurements were performed at 25° C. using a VP-ITC calorimeter (Microcal, Inc.). The ITC cell contained 11 µM detergent-solubilized β$_2$AR or β$_2$AR buffer (blank titration), and the injection syringe contained 70 µM Fab 5. Titrations were initiated with a 3 µl injection, followed by a series of 8 µl injections (37 β$_2$AR and 31 for β$_2$AR buffer blank), with 240 s between injections. After subtracting the blank titration, the measured heat released upon binding was plotted against the Fab: β$_2$AR molar ratio, and the data were fitted to a single-site binding model to obtain the association constant Ka, enthalpy change ΔH, and stoichiometry n using the Origin software package[1] (Microcal, Inc.)

Fab 5 fragments were generated from purified antibody 5 by papain cleavage and purified by ion exchange chromatography. The dissociation constant for Fab 5 binding to purified $\beta_2AR$ was determined to be 150 nM by isothermal titration calorimetry (FIG. 5). As expected, this value is higher than the EC50 (23 nM) observed for the intact antibody in the fluorescence experiments (FIG. 2B).

To localize the intracellular epitope of the $\beta_2AR$ that interacts with Fab 5, limited tryptic digestions of purified $\beta_2AR$ were performed. Cleavage of purified $\beta_2AR$ with trypsin yielded two bands with molecular weights of approximately 27 and 29 kDa on a Western blot probed with the M1 anti-FLAG antibody (FIG. 3A). The sizes of these fragments indicate trypsin digestion at two of ten potential sites in IC3 (FIG. 3A). When preincubated with Fab 5, the 27 kDa band disappears suggesting that the antibody binds to one of the amino-terminal trypsin sites in IC3 (FIG. 3A).

The effect of Fab binding on ligand binding properties and on agonist-induced three dimensional changes was determined. Fab 5 had no significant effect on antagonist or agonist binding affinity (Table 1 below).

TABLE 1

Antagonist and agonist binding properties of the $\beta_2AR$ with and without prebound Fab 5. Saturation and competition binding assays were performed on purified $\beta_2AR$ reconstituted in phospholipid vesicles in the absence and presence of prebound Fab 5. Values are from three independent experiments performed in triplicate.

|  | [$^3$H]dihydroalprenolol $K_d \pm$ S.E. (nM) | Isoproterenol $K_i$ [S.E. interval] (nM) |
|---|---|---|
| $\beta_2AR$ | 1.02 ± 0.09 | 290 [269-311] |
| $\beta_2AR$-Fab5 | 1.08 ± 0.05 | 329 [310-348] |

The IC$_{50}$ values used for calculations of K$_i$ values were obtained from means of pIC$_{50}$ values determined by nonlinear regression analysis and the S.E. interval from pIC$_{50}$ ± S.E.

IC3 is known to be important for G protein activation. Fab 5 prevented coupling of purified $\beta_2AR$ to purified G protein (data not shown), most likely due to steric competition. However, it is possible that Fab 5 restricts the conformational changes associated with receptor activation. The effect of Fab binding on agonist-induced conformational changes was determined using a fluorescence-based assay (Yao et al. Nat. Chem. Biol. 2006 2, 417-422).

Purified receptor was reacted with 1:1 equivalent of monobromobimane (mBBr, Invitrogen) in buffer A (100 mM NaCl, 20 mM HEPES, pH 7.5, 0.1% dodecyl maltoside) and incubated overnight on ice in the dark. The fluorophore-labeled receptor was purified right before use by gel filtration on a desalting column equilibrated with buffer B. Fluorescence spectroscopy experiments were performed on a Spex Fluoro-Max-3 spectrofluorometer (Jobin Yvon Inc, NJ) with photon counting mode by using an excitation and emission bandpass of 4 nm. All experiments were performed at 25° C. For emission scans, excitation was set at 370 nm and emission was measured from 430-530 nm with an integration time of 1 s/nm. To determine the effect of Fab5 antibody and drug, three individual labeled protein samples were incubated with antibody (1 µM Fab5) or 100 µM Isoproterenol or both. Emission spectra of the samples were taken after 15 minutes incubation. Fluorescence intensity was corrected for background fluorescence from buffer and ligands in all experiments. The data are the mean±S.E. of two independent experiments performed in triplicate.

Agonist binding induces a change that brings the fluorophore monobromobimane bound to C271 at the cytoplasmic end of TM6 closer to W135 at the cytoplasmic end of TM3 resulting in a decrease in bimane fluorescence. This fluorescence change was not affected by binding of antibody 5 (FIG. 3B). In conclusion, while Fab 5 required a native $\beta_2AR$ to bind, it did not restrict the movement of transmembrane segments involved in ligand binding and agonist activation.

Figure 6:
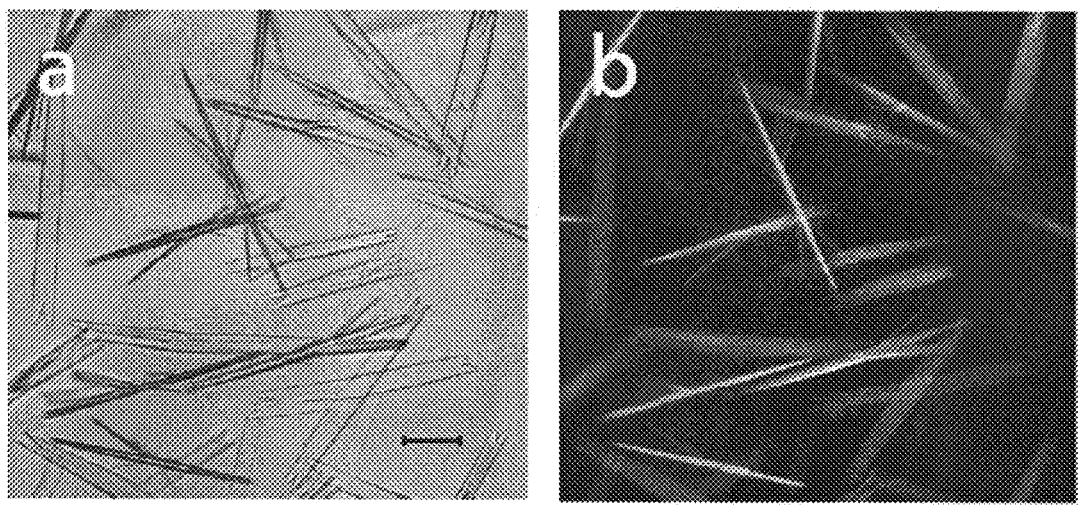
FIG. 6 Image of Fab 5-β$_2$AR-TMR crystals. β$_2$AR was labeled with tetramethylrhodamine (β$_2$AR-TMR) and mixed with an excess of Fab 5. The complex was purified by size exclusion chromatography. Crystals were grown in bicelles and ammonium sulfate (Rasmussen et al manuscript). Images were obtained by light (panel A) and fluorescence (panel B) microscopy. The fluorescence confirms the presence of β$_2$AR-TMR in the crystals. Bar represents 50 µm. All images were acquired using an Axioplan 2 microscope (Carl Zeiss MicroImaging), fitted with a camera (RTE/CCD-1300-Y/HS; Roper Scientific) controlled using IPLab software (BD Bioscience).

To more easily identify crystals of the Fab 5-$\beta_2AR$ complex, we labeled purified $\beta_2AR$ at C265 with tetramethylrhodamine ($\beta_2AR$-TMR). The Fab 5-$\beta_2AR$-TMR complex was formed by mixing $\beta_2AR$-TMR with a stoichiometric excess of Fab 5 and isolating the complex by size exclusion chromatography. Small fluorescent crystals formed by vapor phase diffusion using ammonium sulfate as the precipitant (FIG. 6). Importantly, no crystals formed from $\beta_2AR$ alone or from Fab 5 alone under these conditions, showing that the additional protein interactions and the stabilizing effects of the antibody were critical for successful crystallization of the $\beta_2AR$. Further refinement of the crystallography conditions has since produced diffraction quality crystals and a 3.4 Å structure of the Fab 5-$\beta_2AR$ complex.

EXAMPLE 5

Preparation of Fab Fragments

Monoclonal mouse immunoglobulins against the β2AR reconstituted in liposomes were raised, as described above. Mab5 IgGs from mouse hybridoma cell culture supernatant were purified using a Protein G column (Pierce). Fab5 fragments were generated by papain proteolysis (Worthington) and purified by Mono Q chromatography. The fragments were concentrated to ~100 mg ml$^{-1}$ with a Millipore concentrator (5 kDa molecular weight cut off) in a solution of 10 mM HEPES pH 7.5 and 100 mM NaCl.

EXAMPLE 6

Preparation of β2AR365-Fab5 Complexes

The $\beta_2$AR365 was expressed in Sf-9 insect cells infected with $\beta_2$AR365 baculovirus, and solubilized according to previously described methods. Functional protein was obtained by M1 FLAG affinity chromatography (Sigma) prior to and following alprenolol-Sepharose chromatography. Receptor bound alprenolol was exchanged for carazolol on the second M1 resin. N-linked glycolsylations were removed by treatment with PNGaseF (NEB), and the FLAG epitope was removed by treatment with AcTEV protease (Invitrogen). Protein was concentrated to ~50 mg/ml with a 100 kDa molecular weight cut off Vivaspin concentrator (Vivascience) and mixed in stoichiometric excess of Fab5. The complex was purified on a Superdex-200 (10/300GL) column in a solution of 10 mM HEPES pH 7.5, 100 mM NaCl, 0.1% dodecylmaltoside, and 10 μM carazolol. The purified $\beta_2$AR365-Fab5 complexes were concentrated to ~60 mg ml$^{-1}$ using a Vivaspin concentrator.

EXAMPLE 7

Crystallization

The $\beta_2$AR365-Fab5 complexes were mixed with bicelles (10% w/v 3:1 DMPC:CHAPSO in 10 mM HEPES pH 7.5, 100 mM NaCl) at a 1:5 (protein:bicelle) ratio, and crystals were grown in sitting- and hanging-drop formats at 22° C. using equal volumes of protein mixture and reservoir solutions. Initial crystallization leads were identified using multiple 96-well sitting-drop screens from Nextal (Qiagen). After extensive optimization, crystals for data collection were grown in hanging-drop format over a reservoir solution of 1.85-2.0 M ammonium sulfate, 180 mM sodium acetate, 5 mM EDTA, 100 mM MES or HEPES pH 6.5-7.5. Crystals grew to full size within 7 to 10 days. Crystals were flash frozen and stored in liquid nitrogen, with reservoir solution plus 20% glycerol as cryoprotectant.

EXAMPLE 8

Microcrystallography Data Collection and Processing

Microbeams were employed for data collection. The shape of the crystals permitted complete data to be measured from a single crystal. A small wedge of data, typically 5-10°, (1° per frame) could be measured before significant radiation damage was observed. The crystal was then translated to a new, undamaged position to collect the next wedge of data. A total of 182° of data collected in this manner, measured at beamline ID23-2 of the ESRF, were used for the final $\beta_2$AR365-Fab5 data set (Table 2). The $\beta_2$AR24/365-Fab5 data set was obtained from 225° of data measured on beamline 23ID-B of the APS (Table 2).

TABLE 2

X-ray data collection and refinement statistics

|  | β$_2$AR365-Fab5 | β$_2$AR24/365-Fab5 |
|---|---|---|
| Data collection |  |  |
| Space group | C2 | C2 |
| Cell dimensions |  |  |
| a, b, c (Å) | 338.4, 48.5, 89.4 | 338.4, 48.5, 89.4 |
| α, β, γ (°) | 90., 104.6, 90. | 90., 104.6, 90. |
| Resolution (Å) | 86.4.-3.4 (3.49-3.40)* | 50-3.4 (3.52-3.40)* |
| R$_{merge}$ | 0.117 (0.407) | 0.120 (0.456) |
| I/σI | 9.9 (2.3) | 7.8 (2.6) |
| Completeness (%) | 98.9 (94.9) | 99.4 (98.4) |
| Multiplicity | 3.3 (2.9) | 4.1 (3.4) |
| Refinement |  |  |
| Resolution (Å) | 20.-3.4 | 20.-3.4 |
| No. reflections work/free | 17658/1902 | 17458/1886 |
| R$_{work}$/R$_{free}$ | 0.216/0.269 | 0.226/0.279 |
| No. atoms | 4905 | 4887 |
| Average B values (Å$^2$) |  |  |
| Receptor | 156. | 187. |
| Fab5 | 67. | 91. |
| Overall anisotropic B (Å$^2$) |  |  |
| B$_{11}$/B$_{22}$/B$_{33}$/B$_{13}$ | −27.1/31.3/−4.2/4.4 | −16.8/20.4/−3.5/12.4 |
| R.m.s deviations |  |  |
| Bond lengths (Å) | 0.007 | 0.008 |
| Bond angles (°) | 1.4 | 1.5 |
| Ramachandran plot** receptor/Fab5 |  |  |
| % most favored | 76.3/71.5 | 75.8/71.8 |
| allowed | 22.1/27.2 | 22.1/26.6 |
| generously allowed | 1.6/1.3 | 2.1/1.6 |
| disallowed | 0.0/0.0 | 0.0/0.0 |

*Highest resolution shell is shown in parenthesis.
**As defined in PROCHECK

ESRF data were processed with MOSFLM and SCALA (Collaborative Computational Project, N. Acta Cryst. 1994 D50, 760-763) and data measured at the APS were processed with HKL2000 (Otwinowski et al, Methods Enzymol. 1997 276, 307-326). In many cases it was necessary to reindex the crystal after moving to a new position on the crystal, which may have been due to bending of the frozen crystals such that the indexing matrix from the previous volume could not accurately predict the diffraction pattern from a new volume. This problem precluded global postrefinement of the unit cell parameters. The unit cell parameters used for subsequent analysis (Table 1) were obtained from initial indexing and refinement from one wedge of the ESRF data, and were subsequently found to be sufficient for processing the remaining data without unit cell constant refinement. Using a partial specific volume of 1.21 Å$^3$/Da for protein, the unit cell would have 66% lipid, detergent and aqueous solvent for one β$_2$AR-Fab5 complex in the asymmetric unit. The structure of the β$_2$AR365-Fab5 complex was solved by molecular replacement, by searching with separate constant and variable domain models against a low resolution (4.1 Å) data set measured at ESRF beamline ID-13.

Figure 7:
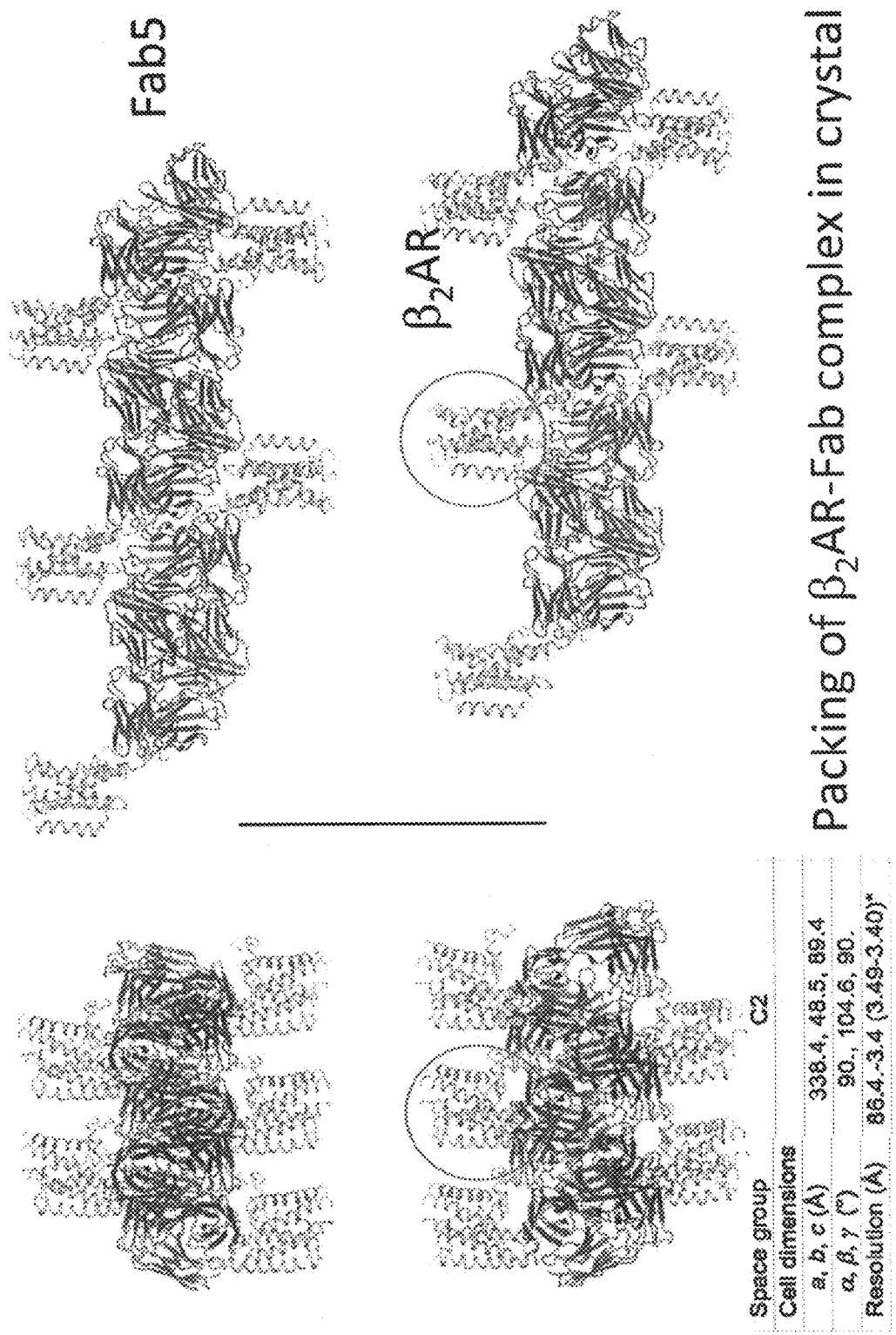
FIG. 7 Figure illustrates packing of β2AR-Fab complex in a crystal.
Figure 8:
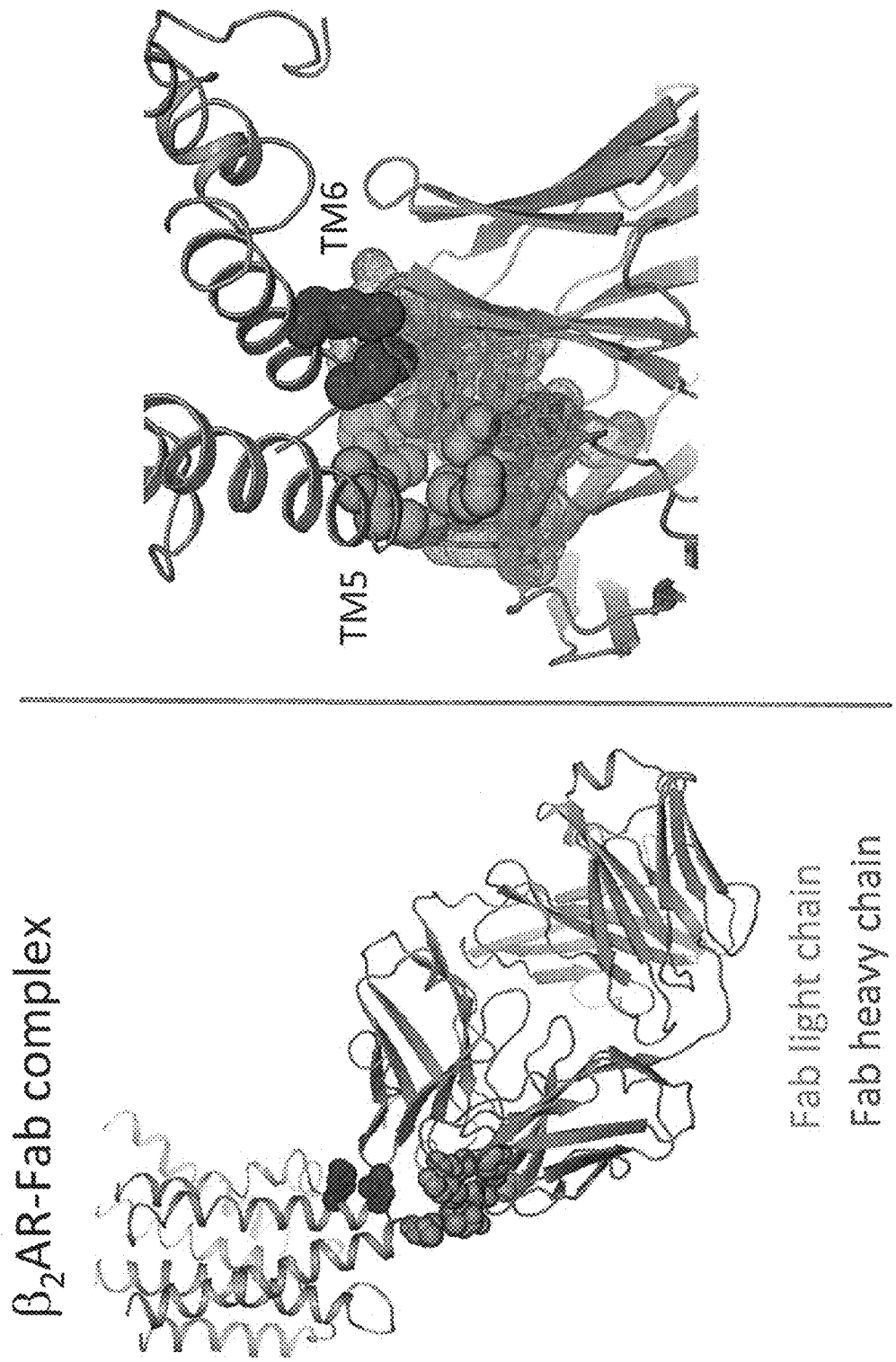
FIG. 8 Figure illustrates the β2AR-Fab complex. As shown, the Fab5 antibody binds a three dimensional epitope that contains amino acids from both ends of the IC3 loop.

The crystal structure confirms that Fab 5 binds to a three dimensional epitope consisting of nine amino acids at the amino-terminal end of IC3 (I233-V242). The antibody also binds two amino acids at the carboxyl-terminal end (L266 and K270), but at a different region of the antibody. FIG. 7 illustrating packing of β2AR-Fab complex in a crystal, and FIG. 8 schematically illustrates the three-dimensional epitope to which the Fab 5 antibody binds.

---

What is claimed is:

1. A method for obtaining crystals of a G protein-coupled receptor (GPCR), comprising:
   a) contacting said GPCR with a monovalent antibody that
      i. specifically binds to a three dimensional epitope of the intracellular region 3 (IC3) loop of said GPCR and
      ii. stabilizes the relative conformations of the transmembrane region 5 (TM5) and transmembrane region 6 (TM6) of said GPCR,
      under conditions that provide for binding of said antibody to said GPCR produce an antibody/GPCR complex;
   b) removing unbound antibody from the product of step a); and
   c) maintaining the product of step b) under conditions suitable for crystallizing said antibody/GPCR complex thereby producing a crystalline form of said antibody/GPCR complex.

2. The method of claim 1, wherein said method comprises combining said antibody/GPCR complex with lipids prior to crystallizing said complex.

3. The method of claim 1, wherein said antibody/GPCR complex is crystallized using a bicelle crystallization method or a cubic-phase crystallization method.

4. The method of claim 1, wherein said GPCR comprises the IC3 loop of the β2 adrenoreceptor (β2AR).

5. The method of claim 1, wherein said GPCR is a chimeric GPCR that contains the IC3 loop of β2AR.

6. The method of claim 1, wherein said GPCR is a chimeric GPCR that comprises amino acid residues I223 to K270 of β2AR.

7. The method of claim 6, wherein said antibody comprises a light chain comprising the amino acid sequence of SEQ ID NO:1 and a heavy chain comprising the amino acid sequence of SEQ ID NO:2.

8. The method of claim 1, wherein the antibody is made by:
   reconstituting a GPCR in artificial phospholipid vesicles to make an antigen;
   immunizing an animal with said antigen; and
   screening a plurality of hybridoma lines obtained from said animal for a hybridoma that produces said antibody.

* * * * *

UNITED STATES PATENT AND TRADEMARK OFFICE
CERTIFICATE OF CORRECTION

PATENT NO. : 7,947,807 B2
APPLICATION NO. : 12/284245
DATED : May 24, 2011
INVENTOR(S) : Brian Kobilka It is certified that error appears in the above-identified patent and that said Letters Patent is hereby corrected as shown below:

- In column 1 lines 10-12: Please replace the paragraph beginning with "This work" to and ending "in this invention." with the follow:

-- This invention was made with Government support under contract NS028471 awarded by the National Institutes of Health. The Government has certain rights in this invention. --

Signed and Sealed this
Twenty-fifth Day of October, 2011

David J. Kappos
*Director of the United States Patent and Trademark Office*